US006337432B1

(12) United States Patent
Dahlman et al.

(10) Patent No.: US 6,337,432 B1
(45) Date of Patent: Jan. 8, 2002

(54) MATERIALS AND METHODS USEFUL TO AFFECT GROWTH AND DEVELOPMENT OF LEPIDOPTERA LARVAE

(75) Inventors: Douglas Lee Dahlman; Bruce Allen Webb; Indu Bhushan Maiti, all of Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/481,161

(22) Filed: Jan. 12, 2000

(51) Int. Cl.[7] ........................... A01H 5/00; C12N 15/82

(52) U.S. Cl. .................... 800/302; 435/320.1; 435/419; 536/23.5; 800/279; 800/288

(58) Field of Search .............................. 435/320.1, 419; 536/23.5; 800/302, 279, 288

(56) References Cited

PUBLICATIONS

Chen et al, Mutations in Domain I of *Bacillus thuringiensis* δ–endotoxin CrylAb Reduce the Irreversible Binding of Toxin to Manduca sexta Brush Border Membrane Vesicles (*), Mar. 1995, Journal of Biological Chemistry, vol. 270, No. 11 pp. 6412–6419.*

M. Peferoen, "Progress and prospects for field use of Bt genes in crops", May 1997, Trends in Biotechnology, vol. 15, pp. 173–177.*

Zhang and Dahlman, 12 *Arch. Insect Biochem. Physiol.* 51 (1989).

Zhang, et al., 43 *J. Insect Physiol.* 577 (1997).

Schepers, et al., 44 *J. Insect Physiol.* 767 (1998).

Zhang, et al., 20 *Arch. Insect Biochem. Physiol.* 231 (1992).

Dong, et al., 32 *Arch. Insect Biochem. Physiol.* 237 (1996).

* cited by examiner

*Primary Examiner*—Elizabeth F. McElwain
*Assistant Examiner*—Cynthia Collins
(74) *Attorney, Agent, or Firm*—McDermott, Will & Emery

(57) ABSTRACT

The present invention provides materials and methods related to causing insect resistance in plants. Specifically, the present invention provides nucleic acid compounds which encode a teratocyte secreted protein (TSP) which is capable of causing inhibition of growth and developmental arrest in Lepidoptera larvae. Cells and plants (including plant parts, seeds, embryos, etc.) comprising the nucleic acid compounds are also within the scope of the present invention. The present invention also provides amino acid compounds encoded by the nucleic acid compounds of the present invention, as well as methods to induce larval developmental arrest, methods to produce the nucleic acid and amino acid compounds, and methods to inhibit crop damage due to Lepidoptera infestation.

9 Claims, 3 Drawing Sheets

Fig. 1. Rabbit reticulocyte lysate assay using luciferase mRNA with the *M. croceipes* 13.9 kDa teratocyte protein generated from a baculovirus expression system. (Each data point is the mean of 4-6 replications, bars = SE).

Expression of TSP in transgenic plants

SEQUENCE LISTING

```
<160> NUMBER OF SEQ ID NOS: 10

<210> SEQ ID NO 1
<211> LENGTH: 320
<212> TYPE: DNA
<213> ORGANISM: Microplitis sp.

<400> SEQUENCE: 1

ccattcgatt tttctgatga tggaaatcaa agctgtgctc cggcttcagg aatctgccat      60

cgagtaggat tagaaattac caaaccgtgt tgtaataaat tcgatcgttg tttcgcttca     120

gtatctgaac ccgtgtctcg ttgtggtggg acggattact cggtagcagt tgtaacagtt     180

ctttcgattg taccaaagtt cagggtgcaa cttgtgaaaa cgggatatgt acttgcggaa     240

aagatgctac tgagtacaca agacacagat gtaaaccaaa tcacatgtcc ccgaaagtta     300

catggtacaa caaaaaatga                                                 320


<210> SEQ ID NO 2
<211> LENGTH: 106
<212> TYPE: PRT
<213> ORGANISM: Microplitis sp.

<400> SEQUENCE: 2

Pro Phe Asp Phe Ser Asp Asp Gly Asn Gln Ser Cys Ala Pro Ala Ser
1               5                   10                  15

Gly Ile Cys His Arg Val Gly Leu Glu Ile Thr Lys Pro Cys Cys Asn
            20                  25                  30

Lys Phe Asp Arg Cys Phe Ala Ser Val Ser Glu Pro Val Ser Arg Cys
        35                  40                  45

Gly Gly Asp Gly Leu Leu Gly Ser Ser Cys Asn Ser Ser Phe Asp Cys
    50                  55                  60

Thr Lys Val Gln Gly Ala Thr Cys Glu Asn Gly Ile Cys Thr Cys Gly
65                  70                  75                  80

Lys Asp Ala Thr Glu Tyr Thr Arg His Arg Cys Lys Pro Asn His Met
                85                  90                  95

Ser Pro Lys Val Thr Trp Tyr Asn Lys Lys
            100                 105
```

-continued

<210> SEQ ID NO 3
<211> LENGTH: 389
<212> TYPE: DNA
<213> ORGANISM: Microplitis sp.

<400> SEQUENCE: 3

```
atgccatcca aaattttaat ttcactcgga atatttctaa ctatttatgt tagttatata     60

tccgctcatc cattcgattt ttctgatgat ggaaatcaaa gctgtgctcc ggcttcagga    120

atctgccatc gagtaggatt agaaattacc aaaccgtgtt gtaataaatt cgatcgttgt    180

ttcgcttcag tatctgaacc cgtgtctcgt tgtggtggga cggattactc ggtagcagtt    240

gtaacagttc tttcgattgt accaaagttc agggtgcaac ttgtgaaaac gggatatgta    300

cttgcggaaa agatgctact gagtacacaa gacacagatg taaaccaaat cacatgtccc    360

cgaaagttac atggtacaac aaaaaatga                                      389
```

<210> SEQ ID NO 4
<211> LENGTH: 129
<212> TYPE: PRT
<213> ORGANISM: Microplitis sp.

<400> SEQUENCE: 4

```
Met Pro Ser Lys Ile Leu Ile Ser Leu Gly Ile Phe Leu Thr Ile Tyr
1               5                   10                  15

Val Ser Tyr Ile Ser Ala His Pro Phe Asp Phe Ser Asp Asp Gly Asn
            20                  25                  30

Gln Ser Cys Ala Pro Ala Ser Gly Ile Cys His Arg Val Gly Leu Glu
        35                  40                  45

Ile Thr Lys Pro Cys Cys Asn Lys Phe Asp Arg Cys Phe Ala Ser Val
    50                  55                  60

Ser Glu Pro Val Ser Arg Cys Gly Gly Asp Gly Leu Leu Gly Ser Ser
65                  70                  75                  80

Cys Asn Ser Ser Phe Asp Cys Thr Lys Val Gln Gly Ala Thr Cys Glu
                85                  90                  95

Asn Gly Ile Cys Thr Cys Gly Lys Asp Ala Thr Glu Tyr Thr Arg His
            100                 105                 110

Arg Cys Lys Pro Asn His Met Ser Pro Lys Val Thr Trp Tyr Asn Lys
        115                 120                 125

Lys
```

<210> SEQ ID NO 5
<211> LENGTH: 17
<212> TYPE: PRT
<213> ORGANISM: Microplitis sp.
<220> FEATURE:
<221> NAME/KEY: UNSURE
<222> LOCATION: (6)..(9)
<223> OTHER INFORMATION: X = unspecified or any amino acid

<400> SEQUENCE: 5

```
Ala Ala Arg Gly Thr Xaa Ala Cys Xaa Thr Gly Gly Thr Ala Tyr Ala
1               5                   10                  15

Ala
```

<210> SEQ ID NO 6
<211> LENGTH: 17
<212> TYPE: PRT
<213> ORGANISM: Microplitis sp.

-continued

```
<220> FEATURE:
<221> NAME/KEY: UNSURE
<222> LOCATION: (9)..(9)
<223> OTHER INFORMATION: X = unspecified or any amino acid

<400> SEQUENCE: 6

Ala Ala Arg Cys Ala Tyr Cys Cys Xaa Thr Thr Tyr Gly Ala Tyr Thr
1               5                   10                  15

Thr


<210> SEQ ID NO 7
<211> LENGTH: 38
<212> TYPE: DNA
<213> ORGANISM: Microplitis sp.

<400> SEQUENCE: 7

gcgggctcga gaccatgggt ccatccaaaa ttttaatt                              38


<210> SEQ ID NO 8
<211> LENGTH: 39
<212> TYPE: DNA
<213> ORGANISM: Microplitis sp.

<400> SEQUENCE: 8

gcgggctcga gaaccatggg tcatccattc gatttttct                             39


<210> SEQ ID NO 9
<211> LENGTH: 45
<212> TYPE: DNA
<213> ORGANISM: Microplitis sp.

<400> SEQUENCE: 9

gcgggctcga gaaccatggg tggatcccat ccattcgatt tttct                      45


<210> SEQ ID NO 10
<211> LENGTH: 42
<212> TYPE: DNA
<213> ORGANISM: Microplitis sp.

<400> SEQUENCE: 10

atgcaggggc tcttaggtcg acccgggccc ttttttcttg ta                         42
```

MATERIALS AND METHODS USEFUL TO AFFECT GROWTH AND DEVELOPMENT OF LEPIDOPTERA LARVAE

BACKGROUND OF THE INVENTION

Parasites of plant-eating insects are natural pesticides. One such solitary parasite, *Microplitis croceipes* (a member of the wasp family Braconidae), causes inhibition of growth and permanent developmental arrest of the tobacco budworm, the cotton bollworm (also known as the corn earworm and tomato fruitworm) and the soybean pod worm. The larvae of these insects (Heliothis and Helicoverpa spp.) feed on tobacco, cotton, maize, sorghum, soybeans, sunflower and tomatoes, among other plants. The larvae cause economic losses of over $1 billion annually, primarily in the form of yield reduction and costs related to control. Fitt, 34 *Ann. Rev. Entomol.* 17 (1989).

In the past, the United States Department of Agriculture has funded programs designed to increase *Microplitis croceipes* populations in Southern states so as to naturally combat these pests in those areas. These efforts were successful in reducing pest populations. Use of such "biomanagement" techniques has generally been replaced with molecular biology techniques, such as those which allowed engineering of plants which express *Bacillus thuringiensis* toxin.

Certain extra-embryonic cells (teratocytes) from *M. croceipes* have been shown to be involved in impairment of the growth, development and related physiological parameters of Heliothis and Helicoverpa larvae. Although teratocytes do not undergo cell division subsequent to their release into the hemocoel of the host, they do become polyploidal. Injection of one larval equivalent of teratocytes caused characteristic post-wandering, pre-pupation developmental arrest and eventual death associated with parasitization. Zhang and Dahlman, 12 Arch. Insect Biochem. Physiol. 51 (1989). Teratocytes collected from *M. croceipes* eggs hatched in vitro produced responses similar to those collected from parasitized Heliothis larvae. Zhang et al., 43 *J. Insect Physiol.* 577 (1997). Furthermore, it has been suggested that when teratocytes are cultured in vitro, they secrete a mixture of proteins (teratocyte secreted proteins or TSP) which, when injected into host larvae, produced responses similar to parasitization. Schepers et al., 44 *J. Insect Physiol.* 767 (1998).

In related studies, juvenile hormone esterase and ecdysone titers have been shown to be suppressed by teratocytes to a degree similar to those in parasitized larvae. Zhang, et al. 20*, Arch. Insect Biochem. Physiol.* 231 (1992). Reduced titers of host hemolymph proteins have been observed, particularly in older stages, with a major effect on the 74, 76 and 82 kD storage protein monomers. Zhang et al., 43 *J. Insect Physiol.* 577 (1997). Inhibition of storage protein synthesis in the fat body was theorized to be at the level of translation, primarily based on the finding that storage protein mRNA levels did not change, even though protein synthesis declined precipitously after treatment with teratocytes. Dong et al., 32 *Arch. Insect Biochem. Physiol.* 237 (1996).

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

It is therefore an object of the present invention to provide isolated nucleic acid compounds useful to inhibit insect larval growth and development.

It is a further object to provide isolated amino acid compounds useful to inhibit larval growth and development.

It is yet another object to provide methods to produce isolated amino acid compounds useful to inhibit larval growth and development.

It is yet another object to provide methods to inhibit larval growth and development.

In all of the above embodiments, it is an object to provide methods to reduce crop damage using the compounds and methods herein.

It is an object of the invention to provide a natural pesticide using the compounds and methods herein.

It is an object of the invention to provide vectors, cells and molecular constructs comprising the compounds and methods herein.

It is an object of the invention to provide plants, including plant parts, seeds and embryos comprising the compounds and methods herein.

Definitions:

For the purposes of the present application, the following terms have the following meanings. All other terms have the meaning as generally recognized in the art.

"Allelic variant" is meant to refer to a gene that occurs at essentially the same locus (or loci) as the referent sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

"Fragment" is meant to refer to any nucleic acid or polypeptide subset of the referent compound.

"Inducing agent" means any compound or condition that causes inducement of an inducible promoter, including chemical compounds or environmental conditions, such as drought, wounds, light cycle, etc.

"Maize" and "corn" shall be interchangeable and mean all maize varieties.

"Proteins" means any compounds which comprise amino acids, including peptides, polypeptides, fusion proteins, etc.

"Transform" means delivery of nucleic acid into a cell, including delivery which results in genomic integration and delivery which results in transient localization within the cell membrane.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified.

An isolated compound of the present invention can be obtained from its natural source, can be produced using molecular biology techniques or can be produced by chemical synthesis.

BRIEF DESCRIPTION OF THE TABLES

Table 1—Sequence listing of cDNAs, peptides and primers.

Table 2—Responses of Heliothis virescens larvae to feeding on transgenic plants expressing the TSP gene.

Table 3—Responses of Manduca sexta larvae to feeding on transgenic plants expressing the TSP gene.

DETAILED DESCRIPTION OF THE INVENTION

Figure 1:
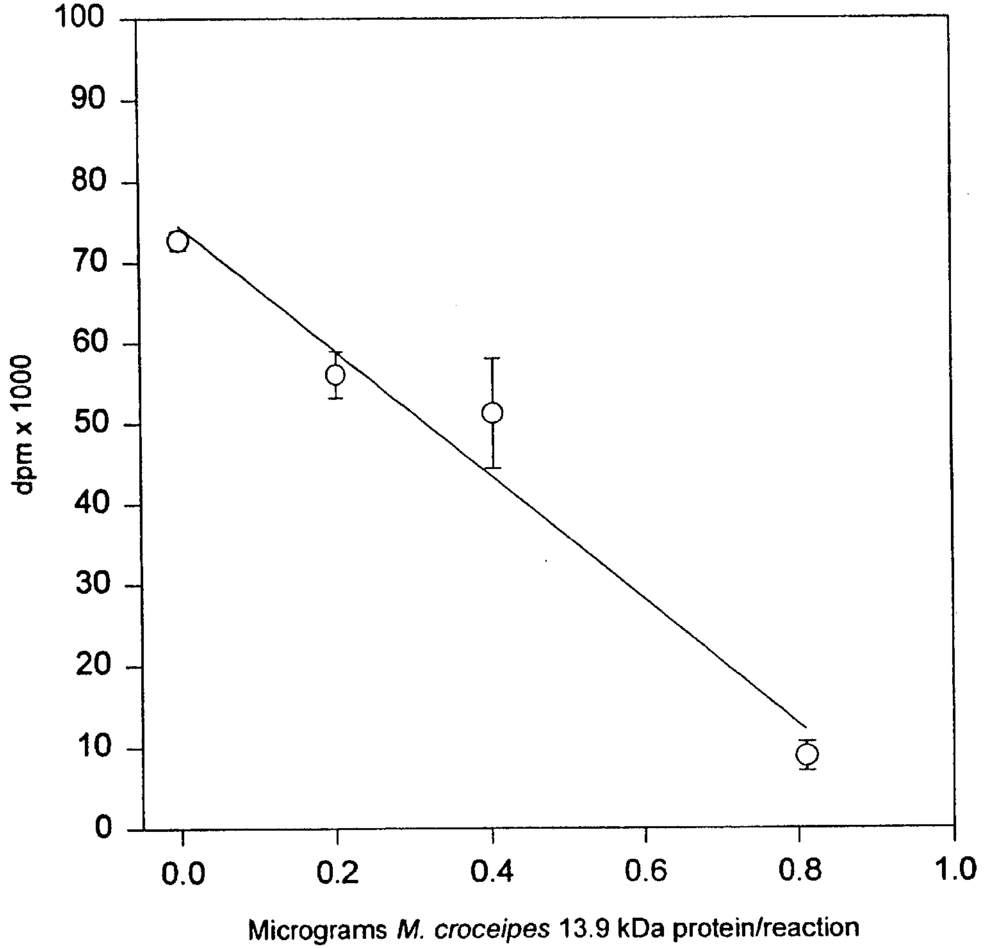
FIG. 1 shows that when the recombinant TSP was tested with a rabbit reticulocyte lysate assay an inverse dose-dependent effect was observed over a range of 0.2–0.8 $\mu$g protein/25 $\mu$L, showing that TSP inhibits protein synthesis.

The present invention provides materials and methods related to causing growth inhibition and developmental arrest of Lepidoptera larvae.

Specifically, the present invention provides nucleic acid compounds which encode a teratocyte secreted protein (named TSP for the purposes of the present invention) which is capable of causing inhibition of growth and developmental arrest of Heliothis larvae. A nucleic acid compound specifically set forth in the sequence listing encodes one such teratocyte secreted protein from *M. croceipes*. The nucleic acid compounds include fragments and complements of the sequence in the sequence listing, as well as sequences which can be obtained, without undue experimentation, by virtue of the knowledge of these sequences. The nucleic acid compounds herein provided therefore include variations on the fragments, complements and other sequences, such as vectors or other constructs containing the fragments, complements, allelic variants and homologues. Cells and plants (including plant parts, seeds, embryos, etc.) comprising the nucleic acid compounds are also within the scope of the present invention.

The present invention also provides amino acid compounds encoded by the nucleic acid compounds of the present invention, as well as methods to induce larval developmental arrest, methods to produce the nucleic acid and amino acid compounds, and methods to reduce crop damage due to a variety of Lepidopteran larval pests, including Heliothis and Helicoverpa species infestations.

Therefore, the present invention provides isolated nucleic acid molecules encoding a TSP protein molecule, wherein said nucleic acid molecule comprises a nucleic acid sequence selected from the group consisting of:

(a) a nucleic acid molecule which has more than 70% identity to a nucleic acid molecule selected from the group consisting of: SEQ ID NO 1 and SEQ ID NO 3, wherein said identity can be determined using the DNAsis computer program and default parameters;

(b) a nucleic acid molecule which encodes an amino acid sequence which comprises an amino acid sequence which has more than 70% identity to an amino acid sequence selected from the group consisting of: SEQ ID NO 2 and SEQ ID NO 4, wherein said identity can be determined using the DNAsis computer program and default parameters;

(c) a nucleic acid molecule which is an allelic variant of a nucleic acid molecule selected from the group consisting of: a nucleic acid molecule of (a); and a nucleic acid molecule of (b); and (d) a nucleic acid molecule fully complementary to a nucleic acid molecule selected from the group consisting of: a nucleic acid molecule of (a); a nucleic acid molecule of (b); and a nucleic acid molecule of (c).

Also provided are vectors, in particular vectors comprising inducible promoters, and for those comprising inducible promoters, in particular those which are tightly regulated. Recombinant plant cells, seeds, plant parts, embryos and plants comprising these vectors are also provided. Preferred are plants selected from the group consisting of tobacco, cotton, corn, soybeans, and tomatoes.

It is well-known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG[a] (available from Genetics Computer Group, Madison, Wis.), DNAsis[a] (available from Hitachi Software, San Bruno, Calif.) and MacVector[a] (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters. A nucleic acid sequence of the present invention may have at least 65%, preferably 70%, and most preferably 90% sequence identity with a nucleic acid molecule in the sequence listing. However, any percent identity within the range of 65 through 100% is within the scope of the present invention. Therefore, molecules with 80%, 85% and 95% identity are also within the scope of the present invention.

Therefore, also provided are isolated nucleic acid compounds encoding a TSP protein molecule, wherein said nucleic acid compound is selected from the group consisting of:

(a) a nucleic acid molecule which has more than 90% identity to a nucleic acid molecule selected from the group consisting of: SEQ ID NO 1 and SEQ ID NO 3, wherein said identity can be determined using the DNAsis computer program and default parameters (b) a nucleic acid molecule which encodes an amino acid sequence which comprises an amino acid sequence which has more than 90% identity to an amino acid sequence selected from the group consisting of: SEQ ID NO 2 and SEQ ID NO 4, wherein said identity can be determined using the DNAsis computer program and default parameters;

(c) a nucleic acid molecule which is an allelic variant of a nucleic acid molecule selected from the group consisting of: a nucleic acid molecule of (a); and a nucleic acid molecule of (b); and (d) a nucleic acid molecule fully complementary to a nucleic acid molecule selected from the group consisting of: a nucleic acid molecule of (a); a nucleic acid molecule of (b); and a nucleic acid molecule of (c).

Also provided are vectors, in particular vectors comprising inducible promoters, and for those comprising inducible promoters, in particular those which are tightly regulated. Recombinant plant cells, seeds, plant parts, embryos and plants comprising these vectors are also provided. Preferred are plants selected from the group consisting of tobacco, cotton, corn, soybeans, and tomatoes.

Also provided by the present invention are isolated nucleic acid compounds comprising a nucleic acid compound which hybridizes under stringent conditions to a nucleic acid molecule selected from the group consisting of:

(a) SEQ ID NO 1 and SEQ ID NO 3.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities -between heterologous nucleic acid molecules. These conditions are well known to those skilled in the art. See, for example, Sambrook, et al., (1989), *Molecular Cloning: A Laboratory Manual*, Cold Spring Harbor Labs Press, and Meinkoth, et al., 138 *Anal. Biochem.* 267 (1984), each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formainide), the average length of the shortest hybrid duplex (n), and the percent G+C composition of the fragment to which an unknown nucleic acid molecule is being hybridized. For nucleic acid molecules of at least about 75 nucleotides or more, these variables are inserted into a standard mathematical formula to calculate the melting temperature, or Tm, of a given nucleic acid molecule. As defined in the formula below, Tm is the temperature at which two complementary nucleic acid molecule strands will disassociate, assuming 100% complementarity between the two strands: Tm=81.5° C.+16.6 log M+0.41(%G+C)−500/n−0.61(% formamide). For nucleic acid molecules smaller than about 50 nucleotides, hybrid stability is defined by the dissociation temperature (Td), which is defined as the temperature at which 50% of the duplexes dissociate. For these smaller molecules, the stability at a standard ionic strength is defined by the following equation: Td=4(G+C)+2(A+T). A temperature of 5° C. below Td is used to detect hybridization between perfectly matched molecules.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of commnon hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect Tm or Td for nucleic acid molecules of different sizes. For example, Tm decreases about 1° C. for each 1% of mismatched base-pairs for hybrids greater than about 75 bp, and Td decreases about 5° C. for each mismatched base-pair for hybrids below about 50 bp. Conditions for hybrids between about 50 and about 75 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides and can therefore choose the appropriate formula for determining hybridization conditions, he or she can determine whether the nucleic acid molecule will hybridize with a given gene under stringent hybridization conditions and similarly whether the nucleic acid molecule will hybridized under conditions designed to allow a desired amount of base pair mismatch.

A preferred isolated nucleic acid compound of the present invention is one which comprises SEQ ID NO 3, with SEQ ID NO 1, or a fragment thereof being most preferred. SEQ ID NO 1 is a most preferred fragment of SEQ ID NO 3. However, an isolated nucleic acid compound which is an approximately 0.9 kb cDNA fragment isolated from *Microplitis croceipes* teratocytes, and which fragment hybridizes to SEQ ID NO 1 or SEQ ID NO 3 under stringent conditions, is preferred.

Included within the scope of the present invention, with particular regard to the nucleic acids above, are allelic variants, degenerate sequences and homologues. Allelic variants are well known to those skilled in the art and would be expected to be found within a given insect, plant or microbe and/or among a group of two or more insects, plants or microbes. The present invention also includes variants of TSP due to laboratory manipulation, such as, but not limited to, variants produced during polymerase chain reaction amplification or site directed mutagenesis. It is also well known that there is a substantial amount of redundancy in the various codons which code for specific amino acids. Moreover, variants of the universal code, such as are present in some plant, animal and fungal mitochondria, the bacterium *Mycoplasma capricolum* [Yamo et al., 82 *Proc. Natl. Acad. Sci.* (*USA*) 2306 (1985)] or the ciliate Macronucleus, may be used when the nucleic acid is expressed using these organisms. Therefore, this invention is also directed to those nucleic acid sequences which contain alternative codons which code for the eventual translation of the amino acid. Methods to mutate genes are well-known to those in the art. Several books, including text books and laboratory manuals are available on the subject. For instance, Sambrook et al., *Molecular Cloning. A Laboratory Manual* (Cold Spring Harbor Laboratory Press, 1989); Ausubel et al., *Current Protocols in Molecular Biology* (Greene Publishing Associates, Inc., 1993) are typical. Moreover, commercial ventures sell kits that have instructions and materials that even those with less than ordinary skill could follow. Kits can be obtained from http://www.sciquest.com, (800) 233-1211.

Also included within the scope of this invention are mutations either in the nucleic acid sequence or the translated protein which do not substantially alter the ultimate physical properties of the expressed protein. For example, substitution of valine for leucine, arginine for lysine, or asparagine for glutamine may not cause a change in functionality of the polypeptide. Lastly, a nucleic acid sequence homologous to the exemplified nucleic acid compounds (or allelic variants or degenerates thereof) will have at least 70%, preferably 80%, and most preferably 90% sequence homology with the nucleic acid compounds in the sequence listing. Most preferred is a mRNA which is complementary to the DNA compounds in the sequence listing. In other words, a mRNA nucleic acid sequence homologous to a DNA nucleic acid sequence is characterized by the ability to hybridize to the exemplified nucleic acid compounds (or allelic variants or degenerates thereof) under stringent conditions. Stringent hybridization conditions, and alterations of amino acids in a polypeptide are well known, and are described, for example, in Sambrook et al., *Molecular Cloning. A Laboratory Manual* (Cold Spring Harbor Laboratory Press, 1989).

A variety of procedures known in the art may be used to molecularly clone the present nucleic acids. These methods include, but are not limited to, complementation for function following the construction of a genomic DNA library in an appropriate vector system. Another method is to screen a genoric DNA library constructed in a bacteriophage or plasmid shuttle vector with a labeled oligonucleotide probe designed from the amino acid sequence of the gene. An additional method consists of screening genomic DNA libraries constructed in a bacteriophage or plasmid shuttle vector with a partial DNA encoding the gene. This partial DNA is obtained by specific PCR amplification of the gene DNA fragments through the design of degenerate oligonucleotide primers from the amino acid sequence of the purified gene product or by using another member of the gene family as a probe. Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993) describe these procedures. Alternatively, the nucleic acids can be prepared as exemplified herein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ. Murray et al., 17 *Nucl. Acids Res.* 477 (1989). Thus, the maize preferred codon for a particular amino acid may be derived from known gene sequences from maize. Maize codon usage for 28 genes from maize plants are listed in Table 4 of Murray et al., supra.

The cloned nucleic acids may be expressed through the methods described in the examples or methods known in the art. The DNA can be recombinantly expressed by molecular cloning into an expression vector containing a suitable promoter and other appropriate transcription regulatory elements, and transferred into prokaryotic or eukaryotic host cells to produce recombinant gene product. Techniques for such manipulations are fully described in Sambrook, et al., supra. Expression vectors can be used to express genes in a variety of hosts such as bacteria, bluegreen algae, plant cells, insect cells, fungal cells and animal cells. Expression vectors may include, but are not limited to, cloning vectors, modified cloning vectors, specifically designed plasmids or viruses.

Vectors which comprise the nucleic acid compounds are within the scope of the present invention, as are plants transformed with the above nucleic acid compounds. Vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.).

Preferred vectors are those which are capable of transferring the sequences disclosed herein into plant cells or plant parts. Expression vectors are preferred, with expression vectors comprising an inducible promoter operably linked to the nucleic acid compound being more preferred. "Inducible" promoters typically direct expression of a polynucleotide in a specific tissue or may be otherwise under more precise environmental or developmental control. The most preferred vectors herein provided are expression vectors comprising a tightly-regulated inducible promoter operably linked to the nucleic acid compound.

Environmental conditions that may effect transcription by inducible promoters include pathogen attack, anaerobic conditions or the presence of light. Examples of inducible promoters are the Adhl promoter which is inducible by hypoxia or cold stress, the Hsp70 promoter which is inducible by heat stress, and the PPDK promoter which is inducible by light. Examples of promoters under developmental control include promoters that initiate transcription only, or preferentially, in certain tissues, such as leaves, roots, fruit, seeds or flowers. An exemplary promoter is the anther specific promoter 5126 (U.S. Pat. Nos. 5,689,049 and 5,689,051). The operation of a promoter may also vary depending on its location in the genome. Thus, an inducible promoter may become fully or partially constitutive in certain locations.

A number of promoters can be used in the practice of the invention. The promoters can be selected based on the desired outcome. For the purposes of the present invention, a wound-inducible promoter may be used in the constructions of the invention. Such wound inducible promoters include potato proteinase inhibitor (pin II) gene (Ryan, 28 *Annu. Rev. Phytopath.* 425 (1990); Duan et al., 14 *Nature Biotech.* 494 (1996); wun1 and wun2, U.S. Pat. Ser. No. 5,428,148; win1 and win2 (Stanford et al., 215 *Mol. Gen. Genet.* 200 (1989); systemin (McGurl et al., 225 *Science* 1570 (1992); WIPI (Rohmeier et al., 22 *Plant Mol. Biol.* 783 (1993); Eckelkamp et al., 323 *FEBS Let.* 73 (1993); MPI gene (Corderok et al., 6 *Plant J.* 141 (1994) and references contained therein. This invention is appropriate for use in all crops potentially attacked by lepidopteran pests. These crops include cotton, maize, soybean, tomato and tobacco.

Promoters as described in the previous paragraphs are also preferred for use in the present vectors. Chemically inducible promoters, such as PR-2b and PR-2d genes which are induced by salicylic acid, can either be constructed de novo according to known techniques, or obtained from various commercial sources, including those described above ,for obtaining vectors. Construction of vectors comprising promoters in frame with nucleic -acids is known in the art, and can be accomplished according to Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993). A general method for the construction of any desired DNA sequence is provided in Brown et al., [68 *Methods in Enzymology* 109 (1979)]. Also provided are vectors comprising rice actin and rice ubiquitin constitutive promoters and the nucleic acid compounds herein. In addition, there are other plant viral promoters which may be used to express genes of the present invention.

Also included in the present invention are recombinant plant cells, recombinant seeds, recombinant plant embryos and recombinant plants comprising the vectors described herein. Seeds, embryos, plants or plant parts which recombinantly express the present amino acid compound(s) or comprise herein-disclosed constructs are preferred embodiments of the present invention. Of course, those in the art recognize that any seed, embryo or plant transformed with the present constructs which are useful for producing plants for biomass are within the scope of the present invention.

Therefore, the present invention includes seeds, embryos, plants or plant parts which recombinantly express an isolated nucleic acid compound, wherein said nucleic acid compound encodes an amino acid compound selected from the group consisting of: SEQ ID NO 4; a fragment of SEQ ID NO 4; an amino acid compound encoded by an allelic variant of a nucleic acid compound encoding SEQ ID NO 4; and a fragment of an amino acid compound encoded by an allelic variant of a nucleic acid compound encoding SEQ ID NO 4. The present invention also provides seeds, embryos, plants or plant parts which recombinantly express isolated nucleic acid compounds comprising a nucleic acid compound which hybridizes under stringent conditions to SEQ ID NO 3.

For example, the following seeds, embryos, plants or plant parts transformed with herein-disclosed nucleic acid constructs are considered within the present invention: rice; soybean; cotton; maize; beet; tobacco; wheat; barley; poppy; rape; sunflower; alfalfa; sorghum; rose; carnation; gerbera; carrot; tomato; egg plant; lettuce; chicory; pepper; melon; cabbage; canola; banana; papaya; casava; fruit and nut trees; tulip; orchid and lilly. Particularly preferred are: tobacco, cotton, maize, soybeans and tomatoes.

Transformation of cells with the nucleic acid compounds of the present invention can be accomplished according to known procedures. For example, infective, vector-containing bacterial strains (such as *Agrobacterium rhizogenes* and *Agrobacterium tumefaciens*) may be used for transformation. Zambryski, 43 *Ann. Rev. Pl. PhysioL Pl. Mol. Biol.* 465 (1992). The following procedures are also well-known: Pollen-tube transformation [Zhon-xun et al., 6 *Plant Molec. Bio.* 165 (1988)]; direct transformation of germinating seeds [Toepfer et al., 1 *Plant Cell* 133 (1989)]; polyethylene glycol or electroporation transformation [Christou et al., 84 *Proc. Nat. Acad. Sci.* 3662 (1987)]; and biolistic processes [Yang & Cristou, *Particle Bombardment Technology for Gene Transfer* (1994)]. The transformed cells are also within the scope of the present invention.

The transformed cells may be induced to form transformed plants via organogenesis or embryogenesis, according to the procedures of Dixon *Plant Cell Culture: A Practical Approach* (IRL Press, Oxford 1987).

In another aspect of the present invention, there is provided isolated TSP protein molecules, wherein said TSP protein molecule comprises an amino acid sequence selected from the group consisting of:

(a) an amino acid sequence encoded by a nucleic acid molecule which has more than 70% identity to a nucleic acid molecule selected from the group consisting of: SEQ ID NO 1 and SEQ ID NO 3, wherein said identity can be determined using the DNAsis computer program and default parameters; and (b) an amino acid sequence which comprises an amino acid sequence which has more than 70% identity to an amino acid sequence selected from the group consisting of: SEQ ID NO 2 and SEQ ID NO 4, wherein said identity can be determined using the DNAsis computer program and default parameters.

Recombinant plant cells and plants comprising the disclosed proteins are also provided. Preferred are those recombinant plants selected from the group consisting of tobacco, cotton, corn, soybeans, and tomatoes.

Isolated TSP protein molecules with 65% to 100% sequence identity to the sequence listing compounds are provided. Indeed, those which are 75%, 80%, 85%, and 95% identical are specifically pointed out as part of the present invention. Moreover, also provided are those isolated TSP protein molecules, wherein said TSP protein molecule comprises an amino acid sequence selected from the group consisting of:

(a) an amino acid sequence encoded by a nucleic acid molecule which has more than 90% identity to a nucleic acid molecule selected from the group consisting of: SEQ ID NO 1 and SEQ ID NO 3, wherein said identity can be determined using the DNAsis computer program and default parameters; and (b) an amino acid sequence which comprises an amino acid sequence which has more than 90% identity to an amino acid sequence selected from the group consisting of: SEQ ID NO 2 and SEQ ID NO 4, wherein said identity can be determined using the DNAsis computer program and default parameters.

Recombinant plant cells and plants comprising the disclosed proteins are also provided. Preferred are those recombinant plants selected from the group consisting of tobacco, cotton, corn, soybeans, and tomatoes.

Most preferred is an isolated amino acid compound which is SEQ ID NO 2, although any portion of SEQ ID NO 2 which has the ability to cause impaired growth and development in lepidoptera larvae is considered part of the present invention as well. Modifications of the amino acid compounds, such as conservative changes in the amino acid sequence, removal of proteolytic cleavage sites to stabilize the peptide, or modifications useful to identify existence or location of gene products are also within the scope of the present invention. For example, an engineered antibody recognition site would be helpful for research purposes, or for quality-control in a commercial plant. Such modifications can be accomplished according to Young et al., [9 *Mol. Plant-Microb. Interact.* 105 (1994)].

The amino acid compounds of the present invention can be purified according to common purification techniques, such as that described in Bollag et al., *Protein Methods* (Wiley-Liss 1996); Scopes, *Protein Purification: Principles and Practice* (Springer-Verlag 1994); Doonan, *Protein Purification Protocols* (Humana Press 1996). For example, artisans will also recognize that these compounds (or portions thereof) can be synthesized by well-known solid phase peptide synthesis or recombinant DNA methods.

For purification via recombinant DNA methods, following expression of the nucleic acids disclosed above in a recombinant host cell, the amino acid compounds described herein can be recovered in purified form. Several purification procedures are available and suitable for use. For example, the amino acid compounds may be purified from cell lysates and extracts by various combinations of, or individual application of salt fractionation, ion exchange chromatography, size exclusion chromatography, hydroxyapatite adsorption chromatography and hydrophobic interaction chromatography. In addition, the amino acid compound can be separated from other cellular proteins by use of an immunoaffinity column made with monoclonal or polyclonal antibodies specific for the full length nascent gene product, or polypeptide fragments of the gene product. Finally, if the vector is modified to include a poly-histidine tag, the expressed protein can be purified by nickel affinity chromatography.

Also provided are methods to construct an insect resistant plant, comprising: introducing into a plurality of plant cells an isolated nucleic acid compound selected from the group consisting of:

(a) a nucleic acid molecule which has more than 70% identity to a nucleic acid molecule selected from the group consisting of: SEQ ID NO 1 and SEQ ID NO 3, wherein said identity can be determined using the DNAsis computer program and default parameters (b) a nucleic acid molecule which encodes an amino acid sequence which comprises an amino acid sequence which has more than 70% identity to an amino acid sequence selected from the group consisting of: SEQ ID NO 2 and SEQ ID NO 4, wherein said identity can be determined using the DNAsis computer program and default parameters; and (c) a nucleic acid molecule which is an allelic variant of a nucleic acid molecule selected from the group consisting of: a nucleic acid molecule of (a); and a nucleic acid molecule of (b); and causing at least some of the plant cells to grow into at least one plant; and selecting those plants which contain the nucleic acid introduced.

Therefore, also provided are formulations for topical pesticides comprising the amino acid compounds herein disclosed. For instance TSP (SEQ ID NO 2) can be used as an ingredient, or alone, in a mixture, suspension, etc. for application directly to Heliothis-infested or potentially infested plants. Alternatively, the TSP gene (either SEQ ID 1 or SEQ ID 3 or modifications thereof) might be used with a recombinant baculovirus insecticide whereby the baculovirus infects the insect and as the virus reproduces it over expresses the TSP gene. Bonning and Hammock, 41 *Ann. Rev. Entomol.* 191 (1996).

In particular, there are provided methods to confer insect resistance properties to a plant, comprising applying to the surface of a plant an isolated nucleic acid molecule selected from the group consisting of:

(a) a nucleic acid molecule which has more than 70% identity to a nucleic acid molecule selected from the group consisting of: SEQ ID NO 1 and SEQ ID NO 3, wherein said identity can be determined using the DNAsis computer program and default parameters (b) a nucleic acid molecule which encodes an amino acid sequence which comprises an amino acid sequence which has more than 70% identity to an amino acid sequence selected from the group consisting of: SEQ ID NO 2 and SEQ ID NO 4, wherein said identity can be determined using the DNAsis computer program and default parameters; and (c) a nucleic acid molecule which is an allelic variant of a nucleic acid molecule selected from the group consisting of: a nucleic acid molecule of (a); and a nucleic acid molecule of (b).

Also in particular, there are provided methods to confer insect resistance properties to a plant, comprising applying to the surface of a plant an isolated amino acid molecule selected from the group consisting of:

(a) an amino acid sequence encoded by a nucleic acid molecule which has more than 70% identity to a nucleic acid molecule selected from the group consisting of: SEQ ID NO 1 and SEQ ID NO 3, wherein said identity can be determined using the DNAsis computer program and default parameters; and (b) an amino acid sequence which comprises an amino acid sequence which has more than 70% identity to an amino acid sequence selected from the group consisting of: SEQ ID NO 2 and SEQ ID NO 4, wherein said identity can be determined using the DNAsis computer program and default parameters.

Moreover, there are provided methods to confer constitutive and/or inducible Lepidoptera resistance to a plant, comprising transforming the plant with a vector comprising the nucleic acid sequences described herein. Since Lepidoptera resistance is one characteristic conferred to a plant by the TSP genes disclosed herein, an ideal method would be to activate the sequences disclosed herein for the amount of time and in quantities necessary to fight the pest, and no longer, since the genes utilize energy that could otherwise be used to create biomass and/or fruit development.

In particular, there are provided methods to confer Lepidoptera resistance in a plant, comprising: transforming at least one plant with a inducible promoter-comprising vector of the present invention, and introducing to the plant an inducing agent capable of inducing the inducible promoter of the vector, and providing the time and conditions needed to cause inducement.

Also provided are methods to induce a Lepidoptera resistance response in a plant transformed with the nucleic acids described herein, comprising: introducing to the plant an agent or environmental conditions capable of inducing the inducible promoter of the vector, and providing the time and conditions needed to cause inducement, and causing inducement. Preferred agents are pathogens, and preferred environmental conditions are wounds. However, it is also within the scope of the present invention to select a plant part into which a vector is transformed, and selectively cause Lepidoptera resistance in response to a developmental stage of the plant, such as upon flowering or at a particular fruit developmental stage. For instance, Heliothis larvae prefer feeding in the growing bud and developing fruit. Resistance could be engineered to coincide with these growing tissues.

Transformation of plants with these sequences would be according to well-known procedures as described above. Plants can be grown according to well-known procedures.

EXAMPLES

Example 1—Insect Populations

Heliothis virescens larvae were reared on artificial diet in a continuous colony maintained at the 25±2° C. with a 16:8

(L:D) photoperiod at the University of Kentucky as described by Vanderzant [55 *J. Econ. Entomol.* 140 (1962)]. Prospective host Heliothis larvae were removed from the colony as pharate fourth instars and parasitized for both colony maintenance and subsequent collection of parasite eggs. Parasitization was accomplished by exposing host larvae for approximately 1 h to mated female *M. croceipes* wasps at a ratio of 8:1. Parasitized larvae were placed into individual cups containing diet and held at 27±2° C. After emergence, the adult parasite wasps were kept at an approximate 1:1 sex ratio and supplied with honey:water (1:1). Zhang et al., 20 *Arch. Insect Biochem. Physiol.* 231 (1992).

Example 2—General Procedures

The in vitro culturing of teratocytes and subsequent collection of the proteins secreted by the teratocytes were described by Schepers et al. [44 *J. Insect Physiol.* 767 (1998)]. Host *H. verescens* larvae were superparasitized by placing 10 larvae and an equal number of wasps in a 15×1.5 cm plastic petri dish which was placed in a lighted incubator at 27° C. for 2 h. Individual superparasitized larvae were placed in 18 mL plastic cups containing diet and held at 27° C. for 28 h. *M. croceipes* eggs were obtained by sterile dissection of superparasitized *H. verescens* larvae 28 h after parasitization. Following surface sterilization by emersion in 95% and 70% ethanol, the larvae were held in sterile water until used for dissection. A larva was placed in a well of a depression slide along with 100 μL of Ex-cell 400 medium (JHR Biosciences, Lexana, Kans.) with 60 μg/mL of gentamicin sulfate. Two fine forceps were used to open the integument without breaking the midgut. The exposed midgut was dipped into the medium and the integument was massaged with forceps to force the *M. croceipes* eggs into the medium. Eggs were collected with a capillary micropipette and washed five times by transfer to fresh sterile 100 μL drops of Ex-cell 400. Ten washed eggs were placed in each of three 100 μL drops of Ex-Cell 400 placed in a 5×0.9 cm tightly sealed Petri dish. The dishes were held in an incubator at 27° C. The eggs hatch approximately 14 h after dissection with each egg yielding approximately 900 teratocytes. Zhang et al. 23 *Int. J. Insect Morphol. & Embryol.* 173 (1994). The teratocytes dissociate from the chorion and begin secreting proteins (TSP). For TSP collection the teratocytes, parasite larvae and medium were placed into microcentrifuge tubes, the parasite larvae were allowed to settle, then the medium and teratocytes were removed with a pipette to a separate microcentrifuge tube which was centrifuged for 5 min at 800×g. The supernatant contained the crude TSP. One larval equivalent (LE) of TSP is that amount (~2 μg of protein) secreted by an in vitro culture of teratocytes derived from a larva during a period of three days. In some cases, the fraction of TSP that passes through a 30 kD molecular weight filter but is retained by a 3 kD filter was used for assays (Schepers et al. supra). The dye-binding Bio-Rad protein reagent (Bio-Rad Laboratories, Hercules, Calif.) was used to determine protein concentrations using bovine serum albumen as a standard assay [Bradford, 72 *Anal. Biochem.* 248 (1976)]. Centricon (Amicon, Inc., Beverly, Mass.) molecular weight cutoff filters were used following the manufacture's directions. SDS-PAGE was performed using a standard method [Laemelli, 227 *Nature* 680 (1970)] and visualized with Coomassie blue and/or silver stain. Southern and northern blots followed standard procedures [Sambrook et al., *Molecular Cloning. A Laboratory Manual*, Cold Spring Harbor Laboratory Press (1989); Ausubel et al., *Current Protocols in Molecular Biology*, Greene Publishing Associates, Inc., (1993)]. Reversed phase HPLC using a 2.1×250 mm VyDac C18 column, 5μ, 300A packing material was used to separate protein components in the 3–30 kD fraction and to separate peptide fractions after hydrolysis of the isolated 13.9 kD protein. The flow rate was 150 μL/min with a binary gradient changing the percentages of 0.06% TFA versus 0.054% TFA in 70% acetonitrile over a 2 h period. Each HPLC peak was collected, concentrated, and subjected to SDS-PAGE.

Example 3—Expression of the 14 kD cDNA

The 13.9 kD protein was purified from approximately 1500 LE of TSP obtained from teratocytes cultured in vitro. Details related to the use of specific procedures cited in this example are described Example 2—General Procedures. The protein of interest passed through a 30 kD molecular weight filter but was retained by a 3 kD filter. Schepers et al., 44 *J. Insect Physiol.* 767 (1998). The 13.9 kD protein was separated from the other 3 TSP proteins in the biologically active fraction by reversed phase HPLC. The most abundant protein (13.9 kD) was selected for the initial analysis. It was digested with the Lys-C protease and rechromatographed on a C 18 column. Two of the fragments were selected for amino acid sequencing using an Applied Biosystems 477A Protein Sequencer. One fragment provided a sequence of only 5 amino acids (VTWYN) while the other fragment was sequenced through 28 positions (PFDFSDDGNOSCAPASGICHRVGLEITK).

To select a cDNA encoding TSP, 2 degenerate primers were synthesized taking advantage of inferred lysine residues N-terminal to the derived peptide sequence (inferred because of Lys-C digestion); terat 1 (SEQ ID NO 5)=AARGTNACNTGGTAYAA; and terat 2 (SEQ ID NO 6)=AARCAYCCNTTYGAYTT. The 3' end and subsequently the 5' end of the cDNA was isolated using the PCR based approach of rapid amplification of cDNA ends [RACE, Frohman IN: Innis PC et al., *PCR Protocols, Academic Press* 28 (1990); Clackson et al. IN: McPherson et al., *PCR: A Practical Approach*, IRL Press, 187, (1991)]. Briefly, an oligo-dT primer (ODT) was used to synthesize cDNA from 1 μg of teratocyte RNA. The degenerate oligonucleotide primers, terat 1 and terat 2, were used in parallel reactions to prime second strand cDNA synthesis then amplified in a conventional PCR reaction (terat 1+ODT and terat 2+ODT). The terat 1+ODT reaction produced a single major amplimer of about 150 bp while the terat 2+ODT reaction produced a major product of approximately 540 bp. The 540 bp amplimer was cloned and sequenced. The signal peptide and untranslated leader sequence were obtained from a 5' RACE product. The composite sequence encodes all 33 amino acids known from peptide sequence data and shows that the terat 2 peptide sequence is N-terminal to the terat 1 peptide, as suggested by the initial amplification products. The complete cDNA contains an open reading frame of 426 nucleotides that encodes a 23 amino acid signal peptide and a total of 129 amino acids with a predicted molecular weight of 14,012. After the removal of the signal peptide, the predicted weight of the secreted protein is 11,466, relatively close to the 13.9 kD molecular weight of the most abundant protein in the 3–30 kD fraction, as estimated by SDS-PAGE. The "inferred" lysine residue used in construction of the terat 2 oligonucleotide was not present in the predicted peptide sequence because this peptide sequence was from the N-terminus of the mature protein. A 17 bp primer-specified poly A tail was preceded by two consensus poly-adenylation signals.

Inspection of the predicted amino acid sequence from the cDNA encoding the 14 kD TSP revealed a cysteine-motif similar to those previously described from a polydnavirus (PDV). Alignment of the TSP-cysteine motif with the 6 motifs from *Campoletis sonorensis* PDV shows that all 6 cysteine residues were conserved at similar spacing to those observed in CsPDVs. A 4 amino acid core (KPCC) was also present in the TSP motif.

The cDNA encoding TSP was expressed only from teratocytes, was encoded by the wasp genome, apparently as a single copy gene, and did not hybridize to the *M. croceipes* PDV genome (T. Schepers and Webb, unpublished). To localize the TSP gene, DNA was extracted from adult male *M. croceipes* wasps and from viral DNA. Two micrograms of viral DNA and 10 μg of male wasp genomic DNA was blotted to nylon membrane in a dot blot apparatus. Cloned TSP was used as a positive control with pZero vector DNA used as a negative control (5 μg each). Only the wasp genomic and positive control DNAs hybridized to the TSP probe. Viral and male wasp genomic DNA were then digested with BamH1 and Xba1 and hybridized under high stringency conditions (50% formamide, 5×SSC, 5×Denhardt's 20 mM Na phosphate with 100 μg/mL sheared salmon sperm DNA at 42° C.) to the TSP probe after electrophoresis on a 0.7% agarose gel and transfer to nylon membrane. Two TSP hybridizing bands were visible on the genomic Southern blot suggesting that the TSP gene exists as a single copy gene in *M. croceipes* chromosomal DNA. The 14 kD cDNA was expressed as a fusion to a polyhistidine tag that simplifies protein purification in both prokaryotic (pET vectors, Novagen) and eukaryotic systems (baculovirus expression system) (BaculoGold, PharMingen). Webb and Summers, 87 *Proc. Nat'l Acad. Sci.* 4961 (1990). An appropriate portion of the amino acid sequence of TSP was synthesized and linked to keyhole lympet hemocyanin and used for antibody preparation.

Southern blots. The TSP cDNA was used to probe DNA prepared from the wasp teratocytes and from *M. croceipes* polydnavirus (McPDV). The TSP cDNA bound exclusively to DNA from the wasp teratocytes.

Molecular analysis of the TSP cDNA. The protein expressed from the baculovirus system was purified for functional analyses. Three different preparations of recombinant TSP were prepared and assessed with the testes assay. A 0.5 μg/100 μL dose of TSP resulted in a 27.1±2.2% (n=11) reduction in protein synthesis by testes. Based on this information and the assumed molecular weight of 11,466, the concentration would be approximately 0.436 μmolar. Three LE of crude TSP used in a parallel set of experiments conducted at the same time yielded a 31.0±6.0% (n=9) reduction in protein synthesis. The control testis of each pair received an equivalent volume of buffer that was identical to that obtained from the TSP preparation.

Example 4—Immunological Analyses

To produce a TSP antiserum, a peptide region of the TSP predicted to have a high degree of antigenicity was synthesized according to the methods described in Harlow and Lane, *Antibodies: A Laboratory Manual*, Cold Spring Harbor Laboratory (1988) and linked to keyhole lympet hemocyanin. Polyclonal antibodies were raised following immunization procedures described by Huebers et al. [158 *J. Comp. Physiol. B* 291 (1988)]. The synthesized peptide was injected into rabbits with an adjuvant. Four weeks after the initial immunization the rabbits were boosted with a similar amount of protein. Two weeks after the primary boost, the antiserum was collected and evaluated with western blots containing the crude TSP and hemoloymph from parasitized insects. Boost immunizations were performed until an antiserum with suitable specificity and titer was produced. Antiserum binding, specificity and reactivity were analyzed by transferring proteins from 16.5% SDS-PAGE gels to Immobilion-P (Milipore; Bedford, Mass.) membranes following the procedure of Li and Webb [68 *J. Virol.* 7482 (1994)] with alkaline phosphatase-conjugated anti-rabbit immunoglobulin G and 4-bromo-4-chloro-3-indolylphosphate p-toluidine salt and nitroblue tetrazolium chloride as chromogenic substrates. In some trials, in order to achieve greater sensitivity, enhanced chemiluminescence with horseradish peroxidase and luminol substrate was used following the instructions provided with the kit (Pierce Chemical Co., Rockford, Ill.).

An immune response was evident to the bacterial TSP, but no protein was detected in either the TSP fractions or in purified TSP from the recombinant virus. However, the antiserum obtained from a rabbit injected with a synthesized region of TSP and linked to keyhole lympet hemocyanin reacted to the protein that has been identified as the secreted TSP. The antiserum will be used for a variety of studies including the localization and function of TSP in host larval tissues and localization of TSP in transgenic plants.

Example 5—Testis Assay

Pairs of testes removed from digging Day 2 (D2) 5th stadium *H. verescens* were processed in a manner similar to the fat body organ culture described by Schepers et al. [44 *J. Insect Physiol.* 767 (1998)]. A single testis of the pair was placed in a total volume of either 50 or 100 μL of methionine depleted medium and a volume of test material. Protein synthesis was measured by [35S]-methionine incorporation during a 4 h incubation. The ratio of cpm from one of the testes pair incubated with the treatment (TSP or candidate fraction) and the other one of the testes pair (control) was used to measure reduction in protein synthesis.

In an assay that used 3 LE of crude TSP/50 μL of medium, we found a significant decrease (82.8±5.4%) in the incorporation of [35S]-methionine in the treated testes compared to the controls (n=25). Schepers et al. supra reported that a significant amount of the activity associated with reduction in protein synthesis in fat body organ assays was confined to the fraction of TSP that passed through a 30 kD filter but was retained by a 3 kD filter. When this fraction was assessed using a rabbit reticulocyte lysate assay with mRNA from *H. verescens* testes, a dose of 3.5 LE/50 μL caused a 51.3±1.4 % decrease in the incorporation of [35S]-methionine (n=3). Although the percentage reduction was less with the concentrated fraction of TSP, it is likely that not all the active component was retained with the fraction, some being lost during the purification process.

Example 6—In Vitro Translation Assays

The effect of TSP on mRNA translation was assessed using a rabbit reticulocyte translation system (Life Technologies, Gaithersburg, Md.). One μg of mRNA was used in a total volume of 25 μL. TSP and buffer controls were concentrated with 3 kD Amicon filters prior to addition to the assay mixture. A wheat germ extract translation system (Promega, Madison, Wis.) also was used to assess the activity of 0.5 μg of TSP in a plant-derived system.

When the recombinant TSP was tested with a rabbit reticulocyte lysate assay an inverse dose-dependent effect was observed over a range of 0.2–0.8 μg protein/25μL (FIG. 1). The concentration of TSP at the highest dose would be approximately 2.79 μmolar.

The wheat germ assay is similar to the rabbit reticulocyte translation system except that wheat germ tissue is used as a source of enzymes, cofactors, etc. It was used to evaluate the effect of TSP mRNA translation in a cell-free system using plant-derived components. In a single experiment with six replications 0.5 µg of TSP significantly reduced [35S]-methionine uptake by 25%.

Example 7—In Vivo Developmental Impairment

Qualitative and quantitative changes in hemolymph proteins in *H. verescens* were observed in larvae injected with either *M. croceipes* teratocytes or crude TSP. Hemolymph protein titers in hosts receiving either 0.5 or 1 LE of teratoctyes were similar to those of parasitized larvae, whereas a single injection of 4 LE of crude TSP was required to induce a similar response. Treated larvae required several days longer than controls to reach a comparable premetamorphic stage [burrowing-digging according to Webb and Dahlman, 2 *Arch. Insect Biochem. Physiol.* 131 (1985)]. Reductions in fat body proliferation similar to those seen in parasitized larvae were observed in larvae treated with either 1 LE of teratocytes, or with 2 or 4 LEs of crude TSP. Proliferation of perivisceral fat body weights from larvae treated with either teratocytes or crude TSP was significantly reduced, in a dose dependent manner, when compared to controls. Both light- and transmission-electron microscopy observations revealed cytological differences in fat body tissues of larvae injected with either teratocytes or crude TSP from the condition observed in parasitized larvae and noninjected controls. Gross dissection of perivisceral fat body from parasitized, teratocyte-injected and TSP-injected larvae showed tissue much less developed and differed considerably in appearance from controls. Observed differences included reduced size and/or number of lipid bodies and qualitative and quantitative changes in other cytoplasmic organelles [Zhang et al., 43 *J. Insect Physiol.* 577 (1997)].

Example 8—Expression of Teratocyte Secretory
Protein (TSP) Gene in Transgenic Plants Renders
Resistance to Insect Feeding Experimental Protocol:

Plant and enzymes: Tobacco plants (*Nicotiana tabacum* CV Samsun NN) were used for plant transformation. Transgenic tobacco seeds (Rl and R2 progeny) were germinated in the presence of Kanamycin (220 µg/mL) for selecting transformed seedlings. Restriction enzymes, DNA modifying enzymes, and DNA and RNA isolation kits were purchased from commercial sources from Gibco-BRL Life Technologies (Rockville, Md.) and used according to the manufactures' specifications. Nitrocellulose membranes for hybridization analysis were obtained from Schleicher & Schuell (Keene, N.H.).

Construction of plant expression vectors pK117, pK118 and pK119: The plasmid pVL1392-TSPhis containing the cDNA gene of teratocyte secretory protein (TSP) from *Microplitis croceipes*, a member of the Braconidae wasp family, was used as starting genetic material. The DNA fragments corresponding to the coding sequence of TSP with and without its signal peptide (TSPdSP) were isolated by PCR amplification from the plasmid pVL1392-TSPhis. For PCR reaction, to isolate TSP with its signal peptide, the following primers were used: a 39-mer forward primer, (named 5'TSP#88) (SEQ ID NO 7), 5'-d(GCGGG CTCGAGACCATGGGTCCATCCAAAATTTTAATT)-3' with 18nt complementary to the 5' end of the TSP gene coding region (amino acid coordinates #2 to 7 of TSP), and XhoI and NcoI restriction cleavage sites (underlined) and translation initiation codon (bold); a 42-mer reverse primer, (named 3'TSP#90) (SEQ ID NO 10) 5'-d(ATGCAG GGGCTCTTAG GTCGACCCGGGCCCTTTTTTCTTGTA)-3' with 18 nt complementary to the 3' end of the TSP gene (amino acid coordinates #126 to 131 of TSP), flanked with two restriction sites SalI and SstI and a stop codon (bold). These restriction sites were introduced into the PCR amplified TSP gene fragment for cloning facilities in plant expression vectors.

Figure 2:
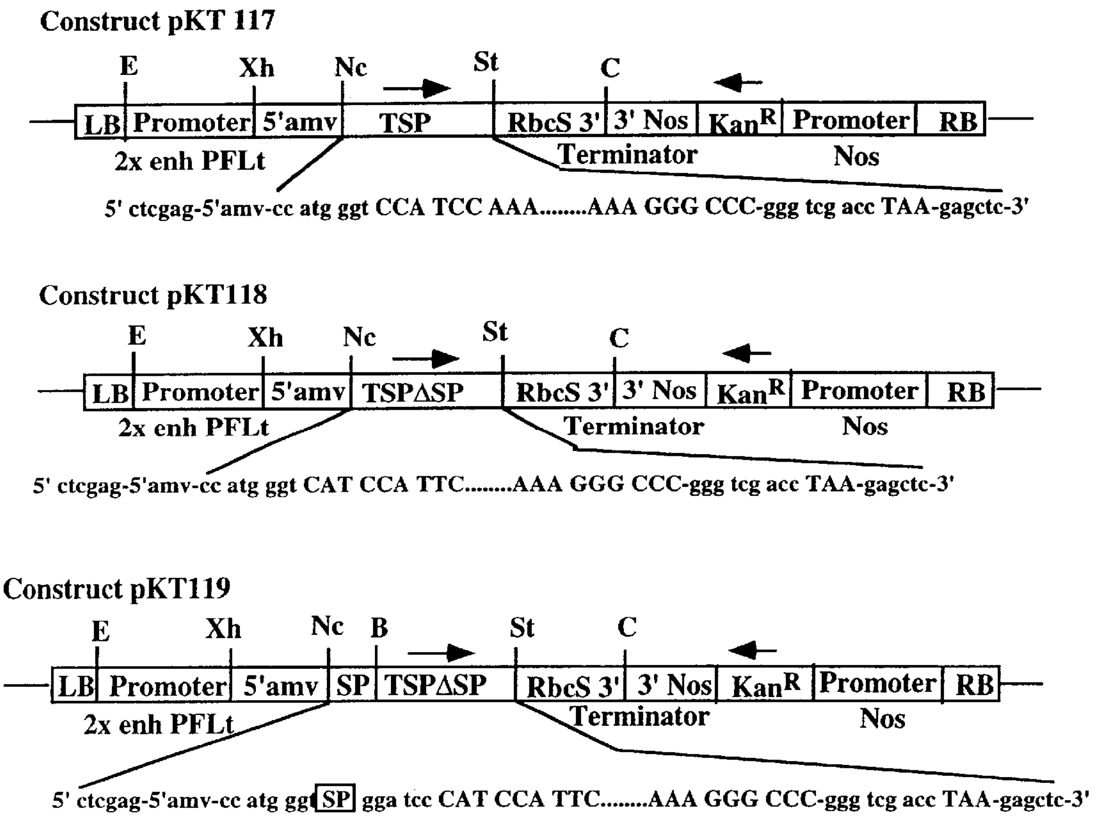
FIG. 2 shows a schematic map of the plant expression vectors constructed for expressing the chimeric TSP gene with its own signal peptide (pKT117) and without any signal peptide (pKT118); and with signal peptide from the PR1b protein (pKT119), showing the coding sequence directed by the peanut chlorotic streak virus full-length transcript promoter (2×enh PFLt), one modified with double enhancer domains [Maiti and Shepherd 244, *Biochem. Biophys. Res. Comm.* 440 (1998); Maiti and Shepherd, U.S. Pat. No. , 5,850,019.

For PCR amplification of the TSP gene without its signal peptide a 39-mer forward primer: (named 5'TSPdSP#89) (SEQ ID NO 8), 5'-d(GCGGGCTCGAG AACCATGGGT CATCCATTCGATTTTTCT)-3' with 18 nt complementary to the 5' end of the TSP gene (amino acid coordinates #23 to 28 of TSP), and XhoI and NcoI sites (underlined) and a translation initiation codon (bold); and the reverse primer, 3'TSP#90 described above were used. The PCR amplification was carried out for 30 cycles under the following standard condition: denaturation (92° C. for 1 min), annealing (55° C. for 1 min), synthesis (72° C. for 2 min). The PCR generated TSP gene fragment, with and without the signal peptide, were digested with XhoI and SstI, gel purified and cloned into the corresponding sites of pBS (KS+) for DNA sequencing. The resulting plasmids were named pBT and pBdT, respectively. Before use, all PCR products were sequenced by dideoxy chain terminator method [Sanger et al., 74 *Proc. Nat'l. Acad. Sci. USA* 5463 (1997)] using a synthetic primer. The TSP fragments with and without the signal peptide were isolated after restriction digestion of pBT and pBdT respectively with NcoI and SstI, the fragments were gel purified and cloned into the corresponding sites of pBS-AlMV5' [Maiti et al., 90 *Proc. Nat'l Acad. Sci. USA* 6110 (1993)] which contains the 5'ut7 untranslated region of AlMV RNA 4. The resulting plasmids were designated as pB5'T and pB5'dT respectively, have the general structure: 5'-XhoI-AlMV-RNA4–5'untranslated region-NcoI-TSP gene fragment-SalI-SstI-3'. The XhoI-SstI fragment of TSP with and without the signal peptide was cloned separately into the corresponding sites of the expression vector pKLP36 [Maiti and Shepherd, 244 *Biochem. Biophys. Res. Comm.* 440 (1998); Maiti and Shepherd, U.S. Pat. No. , 5,850,019 (1998)]. The TSP gene is under the control of a modified PC1SV full-length transcript promoter. The resulting expression vectors were designated as pKT117 (which contains TSP with the signal peptide) and pKT118 which contains TSP without the signal peptide; see FIG. 2).

Construction ofpKT119: The coding sequence (corresponding to amino acid coordinates 23 to 131) of TSP without its signal peptide was isolated by PCR amplification using pVL1392-TSPhis as a template. In PCR reaction the appropriately designed following primers were used. The forward primer (5'TSP#140) (SEQ ID NO 9), 5'-d(GCGGG CTCGAGAACCATGGGT GGATCCCATCCATTCGATTTTTCT)-3' with 18 nt complementary to the 5' end (italic) of the TSP gene (amino acid coordinates #23 to 28 of TSP gene), along with XhoI, NcoI and BamHI sites (underlined) and a translation initiation codon (bold); and the 42-mer reverse primer 3'TSP#90 described above were used. The PCR amplified fragment was gel purified, digested with XhoI and SstI and cloned into the corresponding sites of pBS(KS+). The resulting plasmid was designated as pBdT2. The NcoI to SstI fragment containing TSP without the signal peptide was restricted from pBdT2, gel purified and cloned into the corresponding sites of pBS-AlMV5' [Maiti et al., 90 *Proc. Nat'l Acad. Sci. USA*

6110 (1993)] in order to incorporate the 5'ut7 region of AlMV RNA4 as described above. The resulting plasmid was named as pB5'dT2. A 30 amino acid long transit sequence from PR1b gene was isolated from pBSAPM (a plasmid containing PR 1b transit sequence) by PCR amplification using appropriately designed primers to insert NcoI sites at the 5' end, and BamHI site at the 3' end. The PCR product for transit peptide PR1b was gel purified and digested with NcoI and BamHI and inserted into the corresponding sites of pB5'dT2. The XhoI to SstI fragment from the resulting plasmid pB5'RdT2 was cloned into the corresponding sites of plant expression vector pKLP36 (Maiti and Shepherd supra, supra). The resulting plant expression vector was designated as pKT119.

Plant transformation and analysis of transgenic plants: The plant expression vectors were introduced into *Agrobacterium tumefaciens* strain C58C1:pGV3850 by triparental mating and tobacco (*Nicotiana tabacum* CV Samsun NN) was transformed with the engineered Agrobacterium as described earlier [Maiti et al., 90 *Proc. Nat'l Acad. Sci. USA* 6110 (1993)].

PCR analysis: The integration of TSP gene in the genome of transgenic plants (R1 and R2 progeny) was detected by PCR amplification using appropriately designed primers specific for TSP or TSPASP (TSP without signal peptide) gene sequence. The specificity of each PCR product was analyzed by Southern hybridization with a TSP probe.

RNA isolation, RNA dot blot and Northern analysis: Total RNA was isolated from the transgenic tobacco seedlings (R2 progeny) developed with pKT117 and pKT118 and untransformed control seedlings (Samsun NN). Transformed seedlings developed with pKLP36GUS [Maiti and Shepherd, 244 *Biochem. Biophys. Res. Comm.* 440 (1998)] was used as a vector control. Total RNA was isolated with guanidine thiocyanate solution as described earlier [Maiti et al., 57 *Virus Research* 113 (1998)]. Procedures followed for RNA dot blot and Northern analysis have been described in details (Dey and Maiti, 40 *Plant Mol. Biology*, 71 (1999).

Western blot analysis: Protein was extracted from leaves of transformed plants with TSP constructs and transformed plants with GUS construct as vector control, and nontransformed control plants. Leaf tissue was homogenized in extraction buffer (0.0625M Tris-HCl pH6.8, 10% glycerol, 2% SDS, 10% 2-mercaptoethanol), boiled for 5 min, and centrifuged at 12000×g for 10 min. Total soluble leaf proteins (25 $\mu$g) were separated on a 12.5% SDS-PAGE, transferred to nitrocellulose, and probed with the antiserum raised against the synthetic peptide of TSP. Blots were developed with chemiluminescence reagents from a Pierce kit described above.

Figure 3:
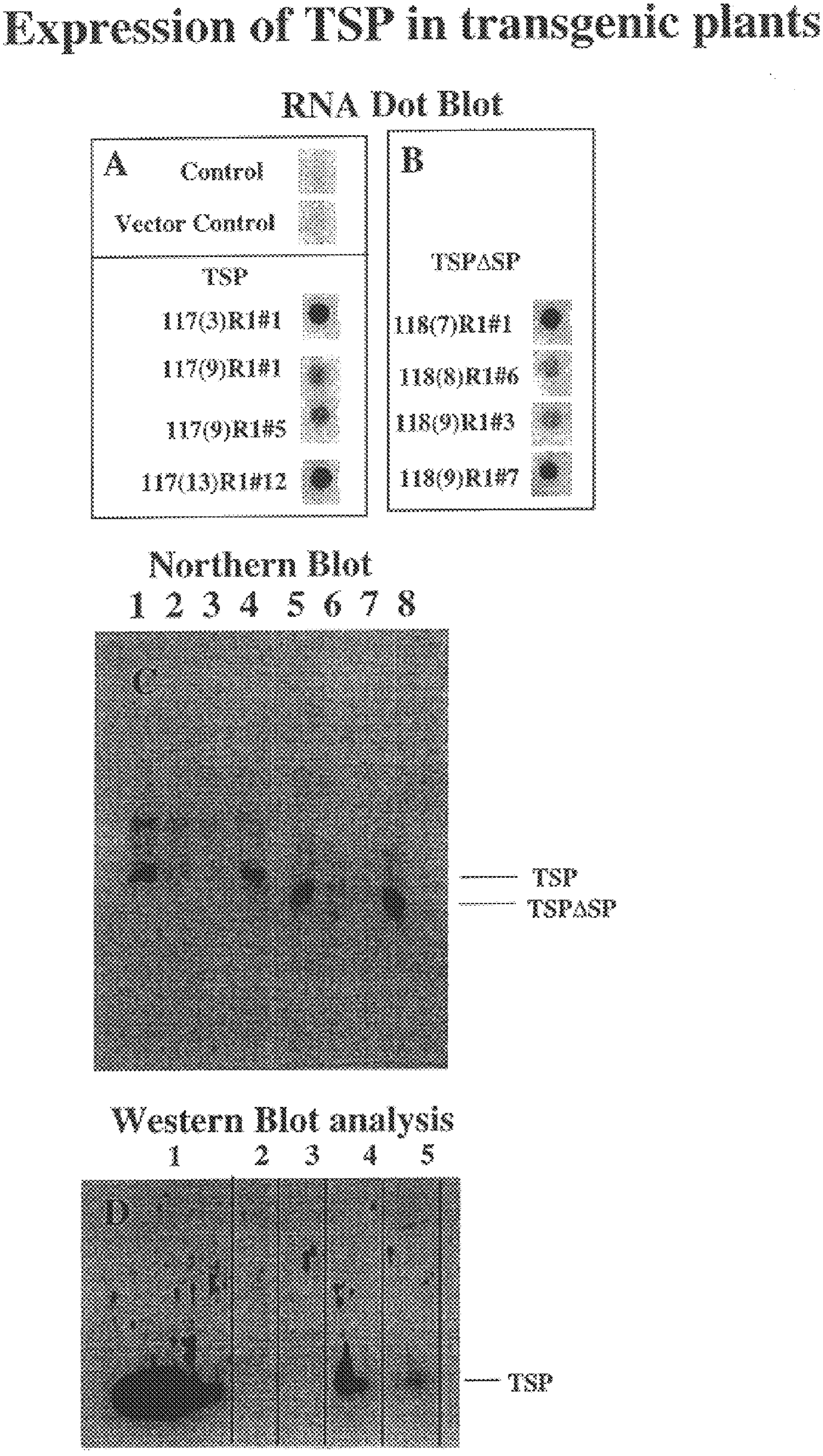
FIG. 3 shows expression analysis of TSP genes in different transgenic plant lines. The RNA Dot Blot shows negative response to control and vector controls but varying levels of RNA in 8 different transgenic plant lines. The Northern Blot shows presence of TSP RNA in lanes 4, 5, and 8. Western Blot analysis contains TSP control in lane 1, control leaf extract in lane 2, control seedling extract in lane 3, transformed leaf extract in lane 4 and transformed seedling extract in lane 5.

Results from the Molecular Analysis of Transgenic Plants:

The chimeric TSP gene with and without its signal peptide were introduced into tobacco plants by Agrobacterium-mediated transformation as described earlier [Maiti et al., 90 *Proc. Nat'l Acad. Sci. USA* 6110 (1993)]. The coding sequence of TSP gene was placed under the control of modified PC1SV FLt promoter and rbcs E9 terminating sequence in the plant expression vector pKLP36 [Maiti and Shepherd, U.S. Pat. No. 5,850,019 (1998)]. The 5' ends of the TSP genes were fused to the untranslated leader sequence of AlMV RNA 4 sequence to enhance the translation of mRNA. The upstream PC1SV FLt promoter was modified with the double enhancer domain in order to stimulate the transcription of chimeric gene in plants [Maiti and Shepherd, U.S. Pat. No. 5,850,019 (1998)]. Transgenic plants derived from each transforment were assayed for the integration and expression of genes by PCR and RT-PCR RNA dot blot and Northern blot and immunobloting analysis. Transgene were stably integrated as shown by PCR analysis for R1 and R2 progeny seedlings (data not shown). Accumulation of TSP mRNA in leaf of transgenic plants were evaluated by RNA dot blot and Northern analysis (FIG. 3). The Northern analysis of total RNA isolated from homozygous lines (R2 progeny/3rd generation) showed the expected size of TSP and TSPΔSP transcripts (FIG. 3).

Proper Mendelian segregation of the KanR marker gene was observed. Homozygous tobacco independent lines (based on KanR marker gene) expressing TSP and TSPΔSP were taken for insect-bioassay.

Example 9—Insecticidal Activity of Transgenic Tobacco Leaf Tissue

Insect bioassays were performed on homologous transgenic lines (R2 progeny) transgenic tobacco plants transformed with the constructs pKT117 and pKT118 containing the TSP with and without its signal peptide, respectively, were tested for insect tolerance by feeding excised leaves to neonate lepidopteran larvae, tobacco budworm (*H. verescens*) and tobacco hornworm (*Manduca sexta*).

The plants to be tested were germinated from seeds on nutrient agar plates, then transferred to nutrient agar placed in the bottom of sterile 6×6×10 cm tall plastic boxes where they were grown under artificial light for approximately four weeks. By this time the plants has attained heights of approximately 10 cm. Leaf material was harvested from these plants, as needed, to supply fresh tissue to each insect in the bioassay.

The assay arena consisted of a 10×50 mm tightly sealed plastic petri dish containing a 4.25 cm disk of Whatman #1 filter paper, moistened with 100 $\mu$L of water. Initially, an approximately 2.5 $cm^2$ portion of leaf tissue was removed from the plant and placed on the moist filter paper. To each dish was added a single neonate *H. verescens* larvae. Ten larvae were used for each treatment. On the third day after the test was initiated, each larva was observed under a dissecting binocular microscope and the developmental stadium was recorded as either being actively feeding or in the premolt or pharate stage of the next stadium. Additional leaf material was added as needed. The width of the head capsule shed after each larval ecdysis was measured at the widest point. Beginning on the fifth day of the test, each larvae was weighed to the nearest 0.1 mg. Also on the fifth day, the contents of the dish and filter paper was replaced. This time the paper was moistened with 75 $\mu$L of water because the mass of leaf tissue added had increased to the point that less supplemental water was required to maintain leaf turgidity. The test was terminated on the seventh day, all larvae were frozen and the ultimate head capsule widths subsequently determined.

A total of 22 transformed tobacco lines have been tested; 11 containing the TSP gene with the signal peptide and 11 containing the TSP gene without the signal peptide. Three different sets of controls were usually included with each group of transformed plants that were tested. These were untransformed tobacco, cultivar Samsun NN; plants transformed with pKLP36GUS, a gene with no known insecticidal activity [Maiti and Shepherd, 244 *Biochem. Biophys Res. Comm.* 440 (1998)]; and artificial diet.

Three different parameters were used to assess insecticidal activity. 1). Weighted values for time to specific developmental stages for days 3, 4, 5, 6 and 7 of the experiment. Even in standardized assays, not all larvae feed and grow at the same rate. Therefore, each developmental stage (instar) was assigned a numerical score as a useful way to statistically evaluate delayed development of *H. verescens* larvae. The following values were assigned: 2nd instar=1, premolt 2nd instar=2, 3rd instar=3, premolt 3rd instar=4, 4th in premolt 4th instar=6, 5th instar=7. 2). Mean weight of larvae on days 5, 6 and 7 of the experiment. 3). Mean width of head capsule (mm) for each instar. The data was analyzed with a one-way AOV and LSD (T) pairwise comparisons of means using a Statistix 4.1 program.

Of the 22 transformed lines tested, six yielded significantly lower values than the GUS control with at least one of the three parameters measured. An additional four lines showed trends that may or may not be statistically different from GUS controls. Table 2 shows that after a seven day feeding trial with selected lines the average developmental stage was approximately one rank less than those feeding on the GUS transformed control. The mean weight gained by larvae in these tests had substantial standard error and only one of the transformed lines yielded significantly reduced weight gain. In three of the lines, head capsule widths were significantly smaller than controls in at least some instars, an indication of less conversion of ingested food to body mass. Four of the six most promising lines were transformed without the signal peptide. However, one of the transformed lines with the signal peptide appears to be one of the better of the group.

Because of limited plant material, only a few tests with larvae of *Manduca sexta* were conducted. The test arena was that same used for *H. verescens* but because neonate *M. sexta* larvae are much larger than *H. verescens* they consume much more leaf material. It appeared that *M. sexta* was much more sensitive to the TSP gene expressed in the transformed plants than *H. verescens* (Table 3). Lines containing the TSP gene without the signal peptide were the most effective. Even though the number of tests was very small, mortality, as well as inhibition of growth and development, was evident within five days after placement on the transformed plant material.

Conclusion

In conclusion, the cDNA encoding TSP, when purified from baculovirus expression systems, inhibits protein synthesis in organ cultures, rabbit reticulocyte lysate assays and wheat germ extract assays. Inhibition of translation was similar to that observed when the 30-kD TSP fraction was assayed. In vivo studies showed that injections of crude TSP caused inhibition of growth, developmental arrest and various physiological changes similar to those caused by injections of teratocytes or parasitization by the *M. croceipes* wasp.

The TSP gene, with and without the signal peptide, has been expressed in transgenic tobacco plants. Heliothis larvae offered some lines of these transgenic tobacco plants grew and developed more slowly than controls. Manduca larvae also grew more slowly and experienced higher mortality than larvae fed control plants.

Although the present invention has been fully described herein, it is to be noted that various changes and modifications are apparent to those skilled in the art. Such changes and modifications are to be understood as included within the scope of the present invention as defined by the appended claims.

TABLE 1

Sequence listing brief description

| SEQ ID NO | Description of Sequence |
|---|---|
| 1 | TSP cDNA sequence (without signal) |
| 2 | TSP amino acid sequence (without signal) |
| 3 | TSP cDNA sequence (with signal) |
| 4 | TSP amino acid sequence (with signal) |
| 5 | Terat 1 |
| 6 | Terat 2 |
| 7 | 5'TSP#88 |
| 8 | 5'TSPdSP#89 |
| 9 | 5'TSP#140 |
| 10 | 3'STP#90 |

TABLE 2

Response of tobacco budworm to transgenic plants expressing TSP gene with and without its signal peptide. Response of neonate *H. virescens* larvae after feeding seven days on transgenic tobacco plants lines.

| Plant Line | Weighted Stage[a] ± S.E. | LSD[b] | Mean Weight ± S.E. (mg) | LSD | % Weight Reduction |
|---|---|---|---|---|---|
| GUS (Control) pKLP36GUS(3)R1#2 | 5.9 ± 0.3 | A | 78.2 ± 10.5 | A | 0 |
| 7311 117(3)R1#3 | 5.3 ± 0.2 | AB | 68.0 ± 8.5 | A | 13 |
| 71019 117(10)R1#9 | 4.8 ± 0.6 | B | 55.6 ± 22.8 | A | 28.9 |
| 8115 118(1)R1#5 | 5.0 ± 0.0 | B | 59.5 ± 10.0 | A | 23.9 |
| 8615 118(6)R1#5 | 4.6 ± 0.8 | B | 47.3 ± 21.1 | B | 39.5 |
| 8711 118(7)R1#1 | 5.2 ± 0.2 | AB | 74.9 ± 10.8 | A | 4.2 |
| 8816 118(8)R1#6 | 5.1 ± 0.4 | B | 69.8 ± 11.8 | A | 11.8 |

[a]Each developmental stage assigned a numerical value with larger values indicating greater developmental rate.
[b]LSD = Least Significant Difference analysis of mean separation. Values followed by the same letter are not significantly different (P ≦ 0.05).

TABLE 3

Response of tobacco hornworm to transgenic plants expressing TSP gene with and without its signal peptide. Response of neonate *M. sexta* larvae after feeding five days on transgenic tobacco plant lines.

| Plant Line | Mean Weight ± S.E. (mg) | LSD[a] | % Mortality at 5 Days |
|---|---|---|---|
| GUS (Control) | 31.8 ± 5.2 | A | 0 |
| pKLP36GUS(3)R1#3 | | | |
| 7311 | 29.4 ± 11.1 | AB | 0 |
| 117(3)R1#1 | | | |
| 8115 | 12.6 ± 2.5 | BC | 50 |
| 118(1)R1#5 | | | |
| 8711 | 9.7 ± 3.3 | C | 25 |
| 118(7)R1#1 | | | |
| 8816 | 8.4 ± 1.3 | C | 50 |
| 118(8)R1#6 | | | |

[a]LSD = Least Significant Difference analysis of mean separation. Values followed by the same letter are not significantly different ($P \leq 0.05$).

We claim:

1. An isolated teratocyte secretory protein (TSP) nucleic acid, wherein said nucleic acid is selected from the group consisting of:

(a) a nucleic acid selected from the group consisting of: SEQ ID NO 1; and SEQ ID NO 3, and (b) a nucleic acid molecule fully complementary to a nucleic acid molecule selected from the group consisting of: SEQ ID NO 1; and SEQ ID NO 3.

2. A vector comprising a nucleic acid of claim 1.

3. A vector of claim 2, wherein said vector further comprises an inducible promoter operably linked to said nucleic acid.

4. A vector of claim 3, wherein said inducible promoter is tightly regulated.

5. A recombinant plant cell comprising a vector of claim 3.

6. A recombinant seed comprising a vector of claim 3.

7. A recombinant plant embryo comprising a vector of claim 3.

8. A recombinant plant comprising a vector of claim 3.

9. A recombinant plant of claim 8, wherein said plant is selected from the group consisting of tobacco, cotton, corn, soybeans, and tomatoes.

* * * * *